United States Patent [19]

Thomenius et al.

[11] 4,208,916
[45] Jun. 24, 1980

[54] ELECTRONIC ULTRASONIC SECTOR SCANNING APPARATUS AND METHOD

[75] Inventors: Kai E. Thomenius, Durham; Richard B. Bernardi, Cheshire, both of Conn.

[73] Assignee: Picker Corporation, Cleveland, Ohio

[21] Appl. No.: 941,919

[22] Filed: Sep. 13, 1978

[51] Int. Cl.² ............................................. G01N 29/04
[52] U.S. Cl. ...................................... 73/626; 73/628; 128/660
[58] Field of Search ................. 73/626, 628, 611, 609; 128/660; 340/5 MP

[56] References Cited

U.S. PATENT DOCUMENTS

| 3,166,731 | 1/1965 | Joy . | |
| 3,373,602 | 3/1968 | Wendt et al. . | |
| 3,723,955 | 3/1973 | Lyons et al. | 340/5 R |
| 3,875,550 | 4/1975 | Quate et al. | 340/5 MP |
| 3,924,259 | 12/1975 | Butler et al. | 340/5 R |
| 4,058,003 | 11/1977 | Macovski | 73/626 |
| 4,116,229 | 9/1978 | Pering | 73/626 |
| 4,152,678 | 5/1979 | Shott et al. | 73/619 |

OTHER PUBLICATIONS

Von Ramm et al., Cardiac Imaging Using a Phased Array Ultrasound System, *Circulation*, vol. 53, No. 2, Feb. 1976, pp. 258-262.

Primary Examiner—Anthony V. Ciarlante
Attorney, Agent, or Firm—Watts, Hoffmann, Fisher & Heinke Co.

[57] ABSTRACT

An electronically scanned phased array diagnostic system for describing internal structure of a subject by the use of ultrasonic energy. The system includes a transducer unit with an array of ultrasonic energy conversion segments and control circuitry for actuating the segments to direct ultrasonic energy into the subject. Imaging circuitry is included for interpreting electrical return signals produced by the segments in response to ultrasonic echoes. The imaging circuitry includes transmission delay circuits for imposing time delays on the return signals for steering and focusing system echo reception. Each transmission delay circuit includes first and second delay elements for impressing first and second delay time components on the return signals. Each pair of the first delay elements are coupled in parallel with separate transducer elements, and serially combined with a downstream second delay element.

The first delay elements provide a portion of the reception steering capability. The second elements provide the remainder of the steering, and the beam focusing, delay components. The system further includes display apparatus responsive to the delayed return signals for producing an image of the subjects internal structure.

17 Claims, 4 Drawing Figures

ELECTRONIC ULTRASONIC SECTOR SCANNING APPARATUS AND METHOD

BACKGROUND OF THE INVENTION

1. Field of the Invention

This invention relates to an improved ultrasonic scanning system used primarily for scanning human tissue to determine its internal structure. A typical ultrasonic scanning unit was a transducer unit for sending and receiving ultrasonic energy. In a transmit mode of operation, the transducer sends incident ultrasonic energy into the patient's body. Variations in tissue density within the patient cause a portion of the ultrasonic energy to be reflected back to the transducer, where the reflected ultrasonic energy is converted into electrical signals. By the use of interpretative imaging circuitry and display apparatus, these electrical signals can be used to display to a diagnostician internal structure within the human body.

The use of multiple segment ultrasonic transducer units with accompanying actuation circuitry enables the examiner to steer and focus the ultrasonic energy to obtain high resolution "pictures" of the internal structure of the human body as that body is being scanned by the steering of the beam. In one such arrangement, a linear array of transducer energy conversion segments comprises the transducer unit. It is possible to selectively phase the actuation of these elements in this array in a known fashion during the transmit mode, according to a predetermined relative sequence, thereby producing a resultant incident ultrasonic beam which can be steered at a given angle with respect to the transducer unit emitting face and which can also be focused at a given fixed distance from that face.

When return echoes are received by an ultrasonic transducer, return focusing circuitry causes the transducer to focus the "listening" or reception portion of operation by selectively enhancing response to signals emanating from certain zones within the subject. This selective listening is achieved by delaying certain return signals relative to each other and then summing those return signals to produce an electronic signal which can be used to produce a visual display on a cathode ray tube or other viewing device. A technique of selectively focusing the return beam is known as "dynamic focusing". In dynamic focusing the zone of enhanced reception is caused to recede coincident with transmission of the incident ultrasonic energy through the patient.

The sending of multiple signals from a multiple element array presents problems with regard to waveform interference within the subject. A point source corresponding to one transducer element produces no interference effects, but a multiple element transducer surface arranged in a linear array approximates a multipoint source of wave energy with accompanying interference characteristics. Multiple point sources of wave energy tend to produce grating lobes or areas of maximum concentration as they propagate away from those sources. In the ultrasonic scanning application, the so-called zero order, or central, lobe is the area of concentration used to scan the subject.

Higher order maxima, or grating lobes, of the incident ultrasonic energy (generated when a resultant beam is produced by a phased transducer segment array) produce interfering spurious return signals. The electronic circuitry of ultrasonic systems is designed to process echo or return signals from the zero order or central lobe, where incident energy is concentrated. Signals returning from the grating lobes therefore create problems in imaging since the circuitry process those return signals as if they were coming from the zero order lobe or area of concentration. It is therefore apparent that this interference from grating lobe echoes degrades the final image quality.

2. Prior Art

One proposal for diminishing the adverse effects of grating lobe interference involves symmetrically reducing transducer element energy propagation about a midpoint in the transducer face. The resulting decrease in grating lobe interference is achieved, however, at the expense of decreasing the scanning resolution capability of the main lobe.

A second proposal reduces grating lobe interference while maintaining uniform energy propagation along the transducer surface. The second proposal achieves the reduction in side lobe interference by a reduction in the transducer element spacing. It is known, for example, that grating lobe interference can not only be reduced, but eliminated, if the transducer elements are spaced closely enough together. All grating lobe interference is eliminated when the spacing between adjacent transducer element midpoints is equal to or less than one half of the wave-length of the emitted sound energy.

Reduction of transducer element spacing, (with consequent increase in the number of elements per unit length) results in substantial increase in the quantity and cost of supporting electronics needed to coordinate both the transducer element firing and the sensing and interpretation of return signals. In a dynamic focusing and beam steering system, this increase is particularly significant, since the receiving electronics in such systems is quite expensive.

In processing return signals, system electronics must be provided to created delays for both (1) beam steering and (2) dynamic focusing. The beam steering delays are linearly related and are analogous to the beam steering delays described in reference to the transmit mode of system operation. They are constant for a particular direction of beam travel and require less sophisticated electronics than are required for producing dynamic focusing delays, which are time-varying and approximately quadratically related. It is thus the electronics necessary to produce dynamic focusing delays, which most significantly increases the system cost when attempting to eliminate grating lobe effects.

Complications are also encountered due in large measure to the fact that the dynamic focusing delays vary with the changing locations of the reception focal zones, i.e., must vary with time. Thus if the echoes are returning from an area fairly close to the transducer within the body the dynamic focusing delays will be relatively short. As the burst recedes deeper into the body the dynamic focusing delays will increase until they reach a maximum delay time.

One technique for providing a time varying dynamic focusing delay involves the utilization of charge coupled devices (CCD's). CCD's are expensive, and each transducer element requires its own charge coupled device and electronic support circuitry to dynamically focus the returning information.

This one-to-one matching of transducer elements with charge coupled devices and supporting circuitry has aggravated the increased cost and complexity required to eliminate the grating lobe interference problem.

SUMMARY OF THE INVENTION

This invention provides apparatus and technique for reducing the cost and quantity of imaging electronics required in an electronically scanned phased array ultrasonic imaging system, notwithstanding the use in that system of a large number of closely spaced transducer elements for ameliorating grating lobe interference.

The present invention is suitably incorporated in an electronically scanned phased array diagnostic system for producing information describing internal structure of a subject by the use of ultrasonic energy. The system includes a transducer unit with an array of ultrasonic energy conversion segments, each segment being capable of converting electrical signals to ultrasonic energy, and reconverting ultrasonic echoes to other electrical signals. The system also includes control circuitry for actuating the segments to direct incident ultrasonic energy into the subject. Imaging circuitry and a display apparatus coupled to the transducer unit produce image representing signals from the electrical echo representing signals and employ the image representing signals to produce a visual image describing internal subject structure.

The imaging circuitry includes delay circuits for imposing beam steering and focusing time delays on the electrical signals generated by the transducer elements. Each delay circuit includes first delay elements electrically connected to a respective different energy conversion transducer elements for producing a first portion of time delay. Each delay circuit also includes a second delay element which is series coupled to a plurality of the first delay elements to combine signals from the first delay elements and provide a second time delay portion for the combined electrical signals.

This delay circuitry, by dividing the impressed delay between first and second delay elements, enables separate control of the delay portions. This feature can enhance system economy by, for example, facilitating the use of relatively inexpensive delay elements to effect a first portion of constant time delay, restricting the use of more expensive variable delay elements to impression of those portions of time delay which must, in fact, be variable. Moreover, the combining of signals from a plurality of first delay elements for processing by a single second delay element obviously "dovetails" the function of each second delay element, reducing the number of such elements required.

In accordance with a more specific aspect of the invention, each delay circuit includes two first delay elements coupled in parallel to adjacent respective energy conversion segments.

In another specific aspect, the first delay elements comprise fixed, or step adjustable delay elements and the second delay elements comprise substantially continuously variable delay elements, for facilitating the selective application of fixed and variable portions of the desired delay.

A further specific feature of the invention involves the use of the first delay elements to effect ultrasonic beam steering delay, while the second variable delay elements effect the remainder of the beam steering delay and also the variable delay required for beam focusing.

It will be appreciated from the foregoing that in a system constructed in accordance with this invention, the number of relatively expensive continuously variable delay elements is reduced in proportion to the number of channels which are combined when compared to prior art systems in which a variable delay element is provided for each and every transducer element. In a system employing a large number of transducer elements which are necessary to reduce side lobe interference, employment of this invention can result in significant saving in the cost and complexity of the delay circuitry and its associated control circuitry.

The advantages of the present invention will be appreciated in more detail by reference to the following detailed description and to the drawings, in which:

DESCRIPTION OF THE PREFERRED EMBODIMENT

Figure 1:
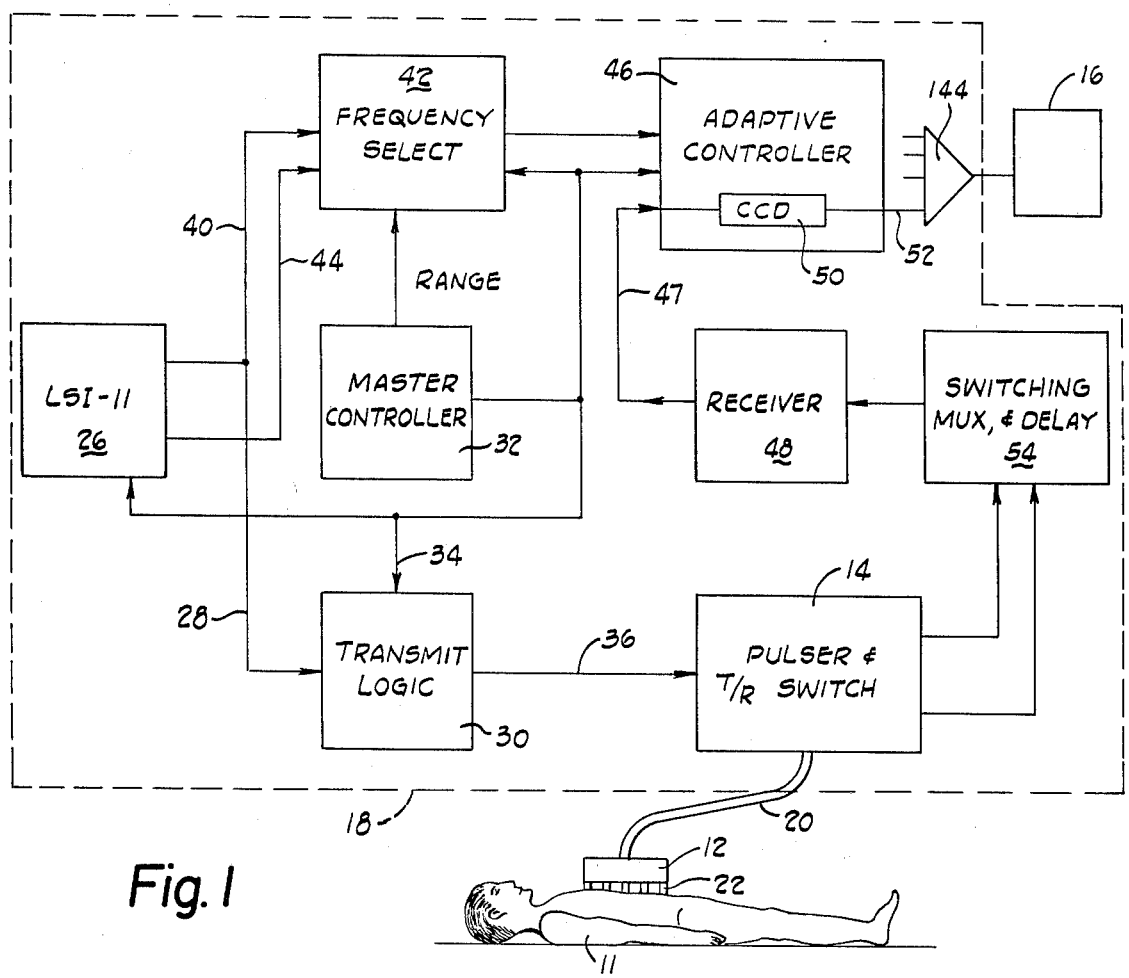
FIG. 1 shows a block and graphical representation of the circuitry of a system embodying the present invention.

FIG. 1 generally depicts a real time electronically scanned ultrasonic imaging system 10 in which an electronically scanned phased array device is incorporated. The system 10 propagates incident ultrasonic energy into a subject, such as a patient 11, and produces substantially instantaneous images of internal body structure of the patient from ultrasonic echoes caused by the incident ultrasonic energy.

The system 10 includes an ultrasonic transducer unit 12 for propagating the ultrasonic energy, display apparatus, generally indicated in the box designated 16, for producing the images, and interposed imaging electronics 18 coupled to the transducer unit 12 by a multi-lead electrical cable 20. The imaging electronics actuates the display apparatus 16 to produce the appropriate visual displays in response to detection of ultrasonic echoes by the transducer unit 12.

The transducer unit 12, of known design, includes a number of individual transducer elements 22, maintained in a side by side substantially linear array by associated mounting structure. One suitable transducer unit has a row of 32 such individual transducer elements. The transducer elements have mutually coplanar ultrasonic energy emitting surfaces.

In operation, the transducer unit 12 is stationarily positioned against a portion of the patient's body, with acoustical coupling being enhanced by the use of a gelatinous acoustic coupling medium between the transducer emitting faces and the patient's body.

Each of the transducer elements comprises a piezoelectric device. Each is individually coupled to the imaging electronics 18 by leads of the cable 20. In this way, transducer elements can be individually actuated, and signals produced by ultrasonic echoes sensed by individual transducer elements can be separately processed. The display apparatus 16 suitably includes a cathode ray oscilloscope and a photographic camera disposed for viewing the cathode ray oscilloscope screen.

In operation, the transducer elements propagate a succession of bursts of ultrasonic energy, each along a respective transmission path, defining an angle $\theta$ (FIG. 2) with respect to the transducer unit face. The transducer elements are resonantly excited at a high frequency (about 1 MHz.—10 MHz.). Echo signals reflected from internal interfaces in the patient's body are received by the transducer elements and used to produce representative electrical signals. The imaging electronics 18, in response, actuates the display apparatus to produce appropriate visual image displays.

The imaging electronics 18 is illustrated in block form in FIG. 1, operatively associated with the transducer array unit 12, with its individual transducer element 22. The imaging electronics controls firing of the transducer elements, and processes signals produced by the transducer elements in response to ultrasonic echoes sensed. The processed signals are then directed to produce images of the patient's internal structure.

The imaging circuitry includes a substantially separate circuitry channel for each transducer element, or segment.

Each channel includes a pulser and switching circuit 14 for firing transducer elements to which it is connected. Each transducer element is coupled to its associated pulser circuit by the switching circuitry. The pulser produces bursts of electrical energy which are directed by the switching circuitry to actuate the associated transducer element to produce a burst of ultrasonic energy incident into the patient 11 along a transmission path.

In operation all elements of the imaging electronics 18 co-operate to steer and focus the ultrasonic beam of energy into the patient 11 and to selectively enhance the returning beam after it has scanned for structural variations inside the patient. Both beam steering and focusing on the transmit portion and dynamic focusing or selective enhancement on the receiver portion require delays to be imposed between individual transducer elements 22.

Delay on the transmit mode or portion refers to delay in pulsing or firing of the respective transducer segments. Delay on the receive mode or portion refers to delay in sending any received signal to the summing circuit 144.

Examples of such a phased linear array real time ultrasonic system and technique, involving steering and focusing of an ultrasonic beam are shown in the following publications, here expressly incorporated by reference: (1) Von Ramm, et. al. "Cardiac Imaging Unit Using a Phased Array Ultrasound System" *Circulation*, Vol. 53, No. 2, February 1, 1976; (2) Walker, et. al., "A Digitally Controlled CCD Dynamically Focused Linear Array", 1975 Ultrasonics Symposium, I.E.E.E. Cat. =CHO-995-USU.

Figures 2, 3:
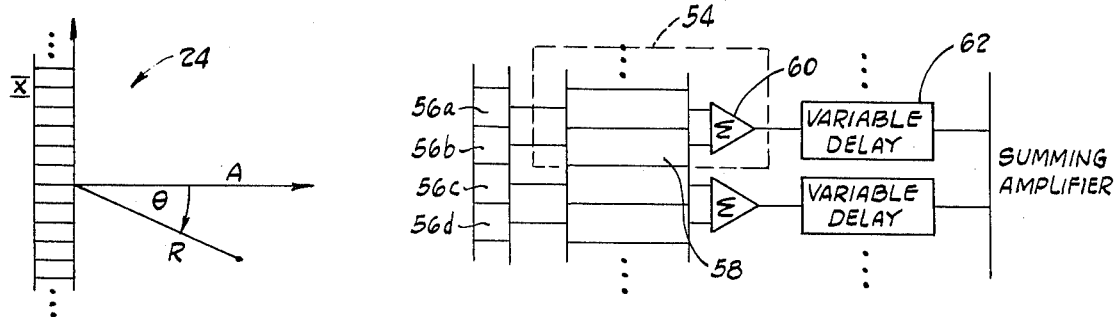
FIG. 2 is a graphical illustration showing a linear array of ultrasonic transducer elements in the present system, with a beam emitted from the face of that transducer.
FIG. 3 is a block diagram of delay circuitry of the system of FIG. 1.

Shown in FIG. 2 is a graphical representation of a typical linear array of ultrasonic transducer elements 24. If the ultrasonic beam is to travel directly away from the face along a path A perpendicular to the array all transducer elements should be pulsed simultaneously. If the beam is to be transmitted along a path at an angle $\theta$ away from the perpendicular, however, time delays must be introduced. If only beam steering is required, uniform delay can be imposed between adjacent transducer element pulsing. This delay is given by the equation D (beam steering)=x sin $\theta$/c, where x is the distance between adjacent transducers, $\theta$ is the angle of propagation as defined in FIG. 2 and C is the speed of sound in the media to be scanned. Uniform delay in pulsing adjacent elements results in a uniform waveform traveling along the path defined by the angle $\theta$.

If one wishes to focus or concentrate the ultrasonic energy at a particular location along that path a position dependent variable delay must be superimposed upon the uniform beam steering delay. A delay which varies as a quadratic function of position along the array when superimposed upon the uniform delay will focus the ultrasonic energy at a point along the beam steering direction. The physical distance from this point of concentration to the transducer array can be altered by changing the quadratic delay function. For a given angle of ultrasonic propagation and for a given point of beam concentration a unique delay function exists which must be utilized in controlling the firing of the transducer elements. As the angle of propagation and focus distance are changed, the delay functions must be altered.

On the receive portion of the scan the delays imposed between adjacent transducer elements are more complex due to the requirement that, even for a fixed $\theta$, they vary with time. From geometrical considerations it can be shown that the difference in arrival time of a wavefront to an element of an array, and the center of the array is given by the equation:

$$D = \frac{1}{c} [R - \sqrt{R^2 - 2R(x)\sin\theta + x^2}]$$

where D=time difference, c=speed of sound in the media, R=distance from origin of wavefront to the midpoint of the array, x is the distance from the midpoint of the array to the element in question and $\theta$ is the angle formed between the vector representation of R and the perpendicular to the array. These parameters are indicated in FIG. 2. It should be stressed that on the receive portion of the scan the waveform originates from a point P within the body and travels to the transducer elements. This point represents a point where a change in density has created an echo or reflection.

As mentioned above the complexity in creating the proper delay on the receive portion is a result of the time variation in this delay. As the ultrasonic wave scans deeper into the body it will create echos from receding depth within the body. Immediately and shortly after the transducer elements are pulsed any returning echoes must be returning from points close to the transducer. As the waveform travels deeper into the body the value of R in the above equation becomes progressively larger. Thus as time passes R changes and the proper delay times imposed upon signals returning to the elements change.

It is mainly this variable delay time imposed upon the receive mode of the scan that necessitates the use of electronics which can be both expensive and complicated.

Details of such electronics can be found in U.S. patent application Ser. No. 889,181 filed Mar. 23, 1978 by R. B. Bernardi and entitled "Dynamically Focused Electronically Scanned Ultrasonic Imaging System and Method" which has been assigned to Picker Corporation, and is expressly here incorporated by reference. From that application and from the above it should be clear that on the transmit portion of the scan the delays between segments for a given scan are constant and depend upon the angle of transmission and the value of the fixed depth of focus. On the receive portion of the scan, however, the delay between segments depends not only upon the angle of transmission but also upon the variable depth from which the echo is returning. For this reason the receive delay between segments relative to a reference segment can be broken into two components; the beam steering delay (determining the angle $\theta$) and the dynamic focus delay. The former is constant for a given scan and the latter varies with time.

The imaging electronics 18 of FIG. 1 can be explained in terms of the beam steering and dynamic focusing delay times. On the left of FIG. 1 is located a microprocessor 26 which controls the sending and receiving of signals of all transducer elements. Since most of the elements of FIG. 1 are known, a functional description will be presented. The microprocessor 26 generates a digital number indicative of the correct beam steering delay for a given transducer element. This number is sent along a first beam steering path 28 to a transmit logic circuit 30. A fixed focus delay number representing the proper delay to focus the transmitted beam at a particular point is added to the beam steering number by the transmit logic circuit 30.

Located directly above the transmit logic circuit 30 in FIG. 1 is a master controller 32. The master controller is a timing signal generator which controls the operation of the other imaging electronic elements. In particular a transmit logic control signal 34 provides a clocking signal telling the transmit logic circuit 30 when to fire the transducers by sending a pulser signal along a lead 36 to the pulser and switching circuit 14. The pulse then sends electrical signals to the piezoelectric material of the transducer element via the multilead cable 20. Thus, through the interaction of the microprocessor 26, the transmit logic circuit 30 and the pulser and switching circuit 14 an ultrasonic beam is transmitted to the body at a predetermined angle and focused at a predetermined distance from the transducer elements.

The dynamic focusing delay times which vary with time on the return portions of the scan are also provided by the imaging electronics 18. The microprocessor 26 sends the beam steering data along a second beam steering data path 40 to a frequency select circuit 42. The frequency select circuit also receives dynamic focusing range information from the master controller. The frequency select circuit combines the two delay time signals to produce one digital frequency control signal indicative of the sum of the proper beam steering and dynamic focus delays. This signal then is sent to an adaptive controller circuit 46 which adds the indicated delay to received signals from the transducer element by synthesizing a proper clocking frequency for a charge coupled delay device.

Circuitry analogous to that of the master controller, the micro processor, the transmit logic and the frequency select circuitry is disclosed in detail in U.S. patent application Ser. No. 879,256 filed Feb. 21, 1978 by Kellogg et al and entitled "Improved Frequency Synthesizer Apparatus and Method in Ultrasonic Imaging", the referenced application being assigned to Picker Corporation and expressly incorporated by reference here.

One technique for providing adaptive controller delays involves the use of charge coupled devices. According to this technique a signal 47 from the transducer element is sent from a receiver unit 48 to the adaptive controller. This signal is converted to a charge in a charge coupled device 50. The change created in the CCD 50 is proportional to the signal transmitted by the receiver. The signal is caused to pass through the CCD at a speed which is dependent upon a clocking frequency provided by the adaptive controller 46. The magnitude of the frequency is in turn dependent upon a frequency select number produced by the frequency select circuit 42. A large number will produce a high frequency with a resultant low delay time as the charge in the CCD is rapidly passed to its output 52.

For a system where delay times are constantly varied as the transit time of return signals changes the adaptive controller or equivalent circuitry can become costly. For this reason the present invention utilizes a switching, multiplexing, and delay circuit 54 to reduce the number of adaptive controllers and charge coupled devices needed within the system.

Shown in FIG. 3 is a schematic representation of the operation of the switching, multiplexing and delay circuit 54 within the imaging electronics. On the left of FIG. 3 are four adjacent transducer elements 56a-d. The return signals to two adjacent exemplary transducer elements 56a and b are received and are transmitted to one switching and delay circuit 54. For illustration purposes it will be assumed the signal arriving at element 56b should be delayed relative to the signal returning to the uppermost element 56a. Ideally this delay should consist of a beam steering delay and a dynamic focusing delay component. Use of the switching and delay circuit 54 has, however, reduced the need for so many adaptive controllers by eliminating the dynamic focus delay between the two adjacent elements 56a and b. The beam steering delay difference between those two elements 56a and b is retained and provided by a delay line within the switching and delay circuit 54. As illustrated in FIG. 3, the signal from the upper element 56a is sent to the switching and delay circuit 54 where it is received by a receiver 58 and sent to a summing circuit 60 where it is combined with the signal from the adjacent element 56b. The adjacent element signal travels to a receiver within the switching and delay circuit 54. This signal, however, is not sent to the summing circuit 60 until a beam steering delay is added to the signal from element 56b. The two signals are summed together in the summing circuit 60 and sent to a variable delay circuit 62 which can conveniently be an adaptive controller with CCD's as delay elements.

Through use of the arrangement depicted in FIG. 3 the number of variable delay circuits 62 has been halved. This savings in circuitry has resulted, however, in slightly different operation of the imaging circuitry. With the configuration shown in FIG. 3, the signals from alternate elements 56a, 56c, etc. receive their total delay for a given scan from a variable delay circuit 62. This delay includes a beam steering and a dynamic focus portion. The delays for the remaining elements 56b, 56d, etc. receive the same delay provided by the variable delay circuit 62 but also receive a portion of their beam steering delay from the constant delay line within the switching and delay circuit 58. This configuration results in each element 56a-d, etc, receiving its own unique beam steering delay on the receive portion of the scan but adjacent elements (56a and b for example), sharing the same dynamic focusing delays. It has been experimentally determined that the image in systems such as described here, in which adjacent elements share dynamic focusing delays, is not substantially degraded from the image produced when each transducer element has its own circuitry for producing dynamic focusing delays.

It is possible to provide a switching arrangement between any suitable N number of elements which would reduce by a factor of 1/N the required dynamic focus electronics for a fixed total number of transducer elements.

Figure 4:
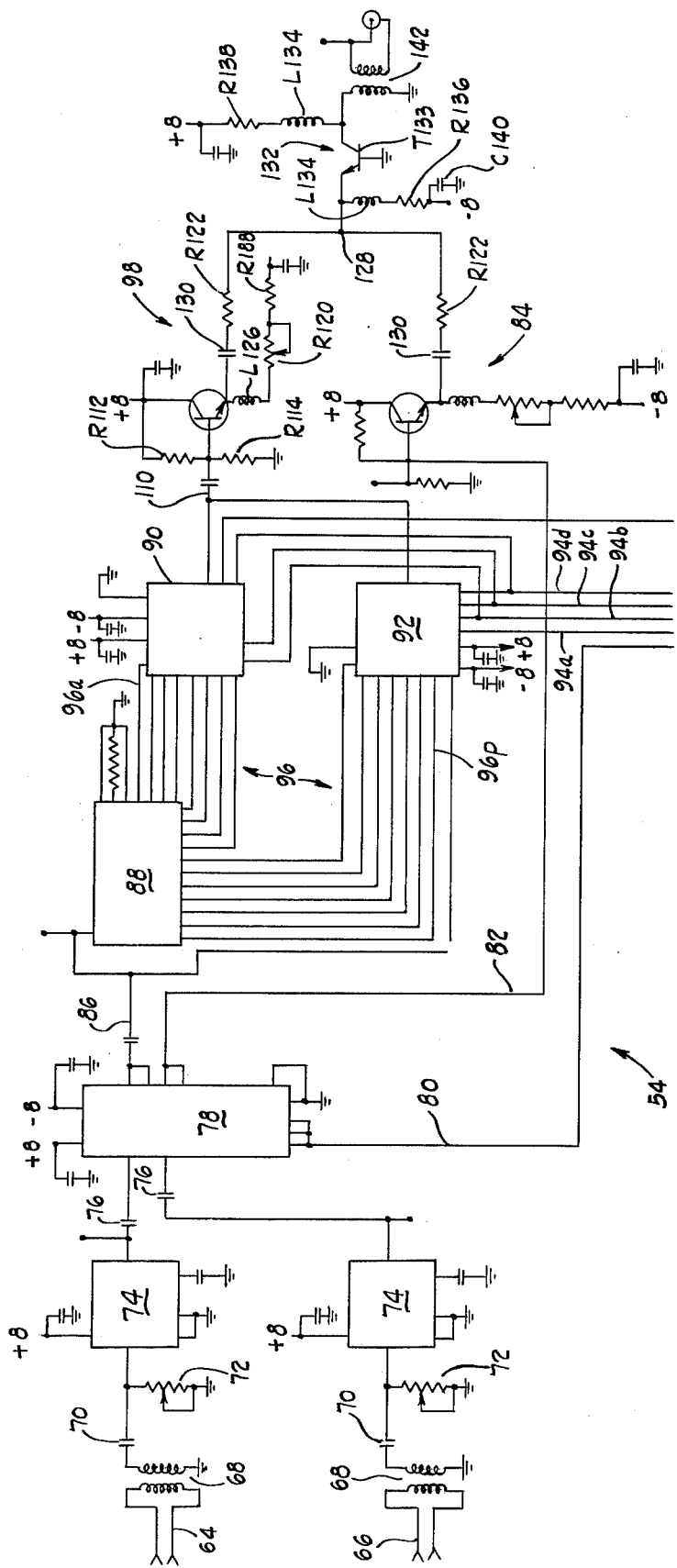
FIG. 4 is a detailed schematic of the delay circuitry of FIG. 3.

Shown in FIG. 4 is an illustrative portion of the circuitry comprising the switching, multiplexing and delay circuit 54 shown schematically in FIGS. 2 and 3. On the extreme left are two input signals 64 and 66 coming from adjacent transducer elements.

When the signals 64, 66 reach input transformers 68 they are undelayed. The signals pass through coupling capacitors 70 which block out D.C. voltages. These signals then pass through rf amplifiers 74 which amplify signals from the transducers. Integrated circuits manufactured by Plessey and bearing parts number SL560C comprising a ring of three amplifier circuits are one circuit which can suitably be used for this function.

After passing a second set of coupling capacitors 76 the as yet undelayed signals reach an analog multiplexer 78. The analog multiplexer determines which of the two signals 64 or 66 is to be delayed relative to the other. This determination is dependent upon the direction which the transmitted signal was sent relative to the transducer surface. In FIG. 2, for example, signals returning to the lower transducer elements must be delayed relative to transducer elements directly above them. If the propagation vector R is above the centerline A, then signals returning to the uppermost elements would have to be delayed relative to the lower transducer elements. Information regarding which of the two input signals 64 or 66 is to be delayed is contained in a multiplexer input 80 which is part of the beam steering data sent from the microprocessor 26. The multiplexer 78 in response to the multiplexer input data sends one undelayed signal 82 to a first emitter follower amplifier circuit 84. This undelayed signal may be either of the two input signals 64, 66 depending upon the direction relative to the transducer array the transmitted beam was sent.

A second signal 86 passes through a coupling capacitor to a lumped constant delay line. One suitable multiplexer would be a Model CD4053 manufactured by RCA Corporation. The amount of time delay to be imposed upon the second signal is controlled by two analog multiplexers 90, 92. Depending upon the condition of a set of digital inputs 94a–d connected to the analog multiplexers 90, 92 one of sixteen possible delay paths 96 from the delay line 88 is chosen to transmit the second signal 86. The sixteen paths represent delays in the second signal of from a minimum delay of 25 nanoseconds extending in equal 25 nanosecond increments to a maximum of 400 nanoseconds in delay. The bottom delay path 96p might, for example, represent a time delay of 25 nanoseconds and the top most path 96a might represent a time delay of 400 nanoseconds.

The condition of the digital inputs 94a–d is controlled by the microprocessor 26 and is a function of the angle of transmittal on the transmit portion of the scan. Thus the delay line 88 under control of the analog multiplexers 90, 92 imposes a time delay on the second signal 86 and sends it to a second emitter follower amplifier circuit 98.

One typical lumped constant delay line which performs the above function is a ESC/124/5 produced by ESC Electronics. The analog muliplexers 90, 92 can suitably be model number CD4051 provided by RCA Corporation.

The emitter follower amplifier circuits 84, 98 perform identical functions on the undelayed 82 and delayed 110 signals. They are follower circuits of known design and merely maintain signal voltage. Suitable component values and part numbers for these circuits are as follows: R112, 1k; R114, 1k; C116 . 1uf; R118 100; R120, 10K; R122, 100; T124, 2N5109. L126, 2.2mh.

The amplified signals must pass through a pair of coupling capacitors 130 and a pair of 100 ohm resistors R122 to a summing junction 128. At that junction the two signals are combined to form one signal. The signal passing through the first emitter follower amplifier circuit 84 is undelayed and the signal passing through the second follower amplifier circuit 98 is delayed from 25 to 400 nanoseconds depending upon the control signals from the microprocessor 26. From the junction 128 the combined signal passes through a common base amplifier 132. That amplifier serves as a low impedance input for the combined signal. Were it not for this low impedance common base amplifier some rebound signal might return along either the delayed or undelayed path causing inaccurate echo signal reproduction. Suitable values for the components of the common base configuration are as follows: T133, 2N5109; L134, 2.2mh; R136, 500; R138, 240; C140, 0.1 u farad.

The combined signal then passes through a transformer 142 the primary winding of which is grounded. From this point the combined signal is sent to a receiver 48 of FIG. 1 where the signal is amplified and sent to the variable delay circuit 62 which might be an adaptive controller utilizing charge coupled devices. At that stage the variable dynamic focus time delays as well as an additional beam steering delay are applied to the combined signal.

As seen in FIG. 1 once the combined signal is provided a dynamic focus delay, it is sent to a summing circuit 144 where the combined signal is added to other signals coming from other transducer elements. The final summed signal is sent to the display apparatus 16 for user interpretation of the echo or received signals returning from the body.

From the above it is clear that the amount of circuitry needed to apply a dynamic focusing delay has been cut in half. Less expensive and less sophisticated constant tapped lumped delay lines provide beam steering difference between adjacent transducer elements while those adjacent elements use identical dynamic focus delay times. The final image representation of internal structure is not degraded while the cost saving is significant.

While the invention has been described with particularity, it should be understood that various modifications and alterations may be made therein without departing from the spirit and scope of the invention set forth in the appended claims.

What is claimed is:

1. An electronically scanned phased array system for producing information describing structure of a subject by the use of ultrasonic energy, said system comprising:
   (a) a transducer unit having ar array of ultrasonic energy conversion segments, said segments capable of converting electrical signals to acoustic energy and re-converting acoustic energy to electrical signals;
   (b) control circuitry for actuating the segments to direct concentrated ultrasonic energy into the subject at a predetermined incident angle;

(c) imaging circuitry coupled to the energy conversion segments for producing images representing electrical signals produced by the segments in response to ultrasonic echoes, said imaging circuitry including transmission delay circuits for imposing time delays on electrical signals from the segments, each transmission delay circuit comprising:
  (i) a first delay element electrically connected to selected conversion segments for producing a first portion of time delay functionally related to the incident angle and for combining the delayed signal with undelayed signals from other of the selected conversion segments, and
  (ii) a second delay element series coupled to the first delay element to provide a second dynamic time delay portion to the electrical signals, and
(d) display apparatus responsive to the image representing signals to produce an image of internal subject structure.

2. The system of claim 1, wherein:
each first delay circuit is coupled to adjacent respective energy conversion segments.

3. The system of claim 1, wherein:
(a) the first delay element comprises a tapped delay line, and
(b) the second delay element comprises a charge coupled device.

4. The system of claim 2, wherein the first element comprises:
a summing circuit having two inputs coupled to the signals from the adjacent respective energy conversion segments and an output connected to the second delay element.

5. A method for describing internal structure of a subject by the use of a phased array electronically scanned ultrasonic system having a transducer unit including an array of ultrasonic energy conversion segments, said method comprising the steps of:
(a) actuating the segments to direct incident ultrasonic energy into the subject;
(b) producing images representing electrical signals produced by the energy conversion segments in response to ultrasonic echoes, by steps including:
  (i) imposing a first time delay portion on selected electrical signals from each of a plurality of segments and
  (ii) combining the first time delayed signals with selected undelayed signals from a second plurality of segments
  (iii) imposing a second time delay portion on the combined signals, and
  (iv) summing all delayed signals, and
(c) producing an image of internal subject structure from the delayed image representing signals.

6. The method of claim 5, wherein:
(a) said first time delay imposing step comprising the imposition of fixed time delays, and
(b) said second time delay imposing step comprising imposition of a time variable time delay.

7. The method of claim 5, wherein:
(a) said first time delay portion comprises a portion of time delay required for steering the direction of reception of ultrasonic echo energy by the segments, and
(b) said second time delay portion comprises:
  (i) the remainder of the steering time delay, and
  (ii) a time delay for focusing the reception of ultrasonic energy by the segments.

8. An ultrasonic diagnostic system comprising:
(a) a transducer including a plurality of energy conversion segments arranged in an array, said segments operative to transmit ultrasound energy in response to electrical pulses and to convert received ultrasound energy into electrical signals, said received ultrasound beams bearing information regarding the internal structure of an object of interest;
(b) control means for selectively causing said segments to emit ultrasonic energy in a controlled sequence thereby producing an ultrasonic waveform aimed in a particular direction and focused at a particular range within the object of interest;
(c) a summing circuit for combining electrical signals from the segments in response to incoming ultrasonic energy;
(d) transmission means operatively interposed between said segments and said summing circuit; said transmission means including a plurality of delay circuits for selectively imposing time delays on the electrical signals in response to information generated within said control means; each delay circuit including a variable delay element for producing one portion of said time delay, and a second delay element for producing time delays fixed for a given scan angle to selected ones of the electrical signals from adjacent segments and summing them for transmittal to the variable delay element; and
(e) display means responsive to the combined electrical signals from the summing circuit to produce a visual image of the internal structure of the object of interest.

9. The system of claim 8, wherein the control means is operative to select which of the signals from the adjacent segments to delay; and wherein said second delay element further comprises a tapped delay line for selectively delaying that signal.

10. The system of claim 9, wherein the variable delay element comprises a charge coupled device; said device operative to receive a signal from the second delay element and delay that signal an amount of time dependent upon the range from which the corresponding incoming ultrasonic energy is originating.

11. An electronic signal processor for summing a plurality of acoustic signals impinging upon a multisegment acoustic transducer surface comprising:
(a) detecting means for converting said signals to a plurality of electrical signals;
(b) a summing circuit for combining said electrical signals;
(c) a plurality of delay means interposed between said detecting means and said summing circuit for delaying the plurality of electrical signals relative to each other; and
(d) said delay means comprising:
  (i) a first delay means operative to delay a first electrical signal from one segment relative to a second electrical signal from a different segment;
  (ii) an intermediate summing circuit operative to combine said first and second signals and produce a third signal; and
  (iii) a second adjustable delay means operative to delay said third signal before said third signal is combined with other electrical signals by said summing circuit.

12. The electronic signal processor of claim 11, wherein the first delay means comprises a lumped constant delay line with a multitude of variable delay settings; said settings operative to delay said first electrical signal a variable amount of time relative to said second electrical signal.

13. The electronic signal processor of claim 12, wherein the second adjustable delay means comprises a charge coupled device; the third signal delay being variable according to a clocking frequency controlling said charge coupled device.

14. A circuit for combining the electric signals from two adjacent acoustic transducer elements comprising:
(a) receiver means to transmit incoming electrical signals;
(b) an analog multiplexer for determining which of two incoming signals is to be delayed;
(c) a summing circuit for combining the delayed and the undelayed signal;
(d) a delay means operatively interposed between the summing circuit and the multiplexer to selectively change the delay in the delayed signal; and
(e) transmission means interposed between the summing circuit and the multiplexer to transmit the undelayed signal to the summing circuit.

15. The circuit of claim 14, wherein the delay means comprises a tapped lumped constant delay line with a multitude of delay taps; each delay tap operation to delay a signal a unique amount of time.

16. The circuit of claim 15, wherein the delay means further comprises selection means controlled by an external control signal source for choosing a suitable delay tap for sending a delayed signal to said summing circuit.

17. The circuit of claim 16, wherein the selection means comprises two analog multiplexers for decoding a signal from the external control signal source and select one of sixteen delay taps on the lumped constant delay line in response to the decoding.

* * * * *

UNITED STATES PATENT AND TRADEMARK OFFICE
CERTIFICATE OF CORRECTION

PATENT NO. : 4,208,916
DATED : June 24, 1980
INVENTOR(S) : Kai E. Thomenius and Richard B. Bernardi It is certified that error appears in the above-identified patent and that said Letters Patent are hereby corrected as shown below:

```
Column 2, line 3, "process" should be -- processes --.
Column 5, line 55, "CHO-995" should be -- CHO-994 --.
Column 7, line 32, "pulse" should be -- pulser --.
Column 10, line 61, "ar" should be -- an --.
```

Signed and Sealed this

Second Day of September 1980

[SEAL]

Attest:

SIDNEY A. DIAMOND

Attesting Officer          Commissioner of Patents and Trademarks